United States Patent
Hirsch et al.

(10) Patent No.: US 12,123,875 B2
(45) Date of Patent: Oct. 22, 2024

(54) ANTIGEN ANALOGUE FOR CALIBRATION OF IMMUNOMETRIC DIAGNOSTIC ASSAYS

(71) Applicant: ORTHO-CLINICAL DIAGNOSTICS, INC., Raritan, NJ (US)

(72) Inventors: Brett Hirsch, Raritan, NJ (US); Jian Zheng, Raritan, NJ (US); Stephen Daggett, Raritan, NJ (US)

(73) Assignee: Ortho Clinical Diagnostics, Inc., Raritan, NJ (US)

( * ) Notice: Subject to any disclaimer, the term of this patent is extended or adjusted under 35 U.S.C. 154(b) by 45 days.

(21) Appl. No.: 17/840,557

(22) Filed: Jun. 14, 2022

(65) Prior Publication Data

US 2022/0404358 A1 Dec. 22, 2022

Related U.S. Application Data

(60) Provisional application No. 63/210,904, filed on Jun. 15, 2021, provisional application No. 63/340,372, filed on May 10, 2022.

(51) Int. Cl.
*G01N 33/566* (2006.01)
*C07K 7/08* (2006.01)

(52) U.S. Cl.
CPC ............. *G01N 33/566* (2013.01); *C07K 7/08* (2013.01); *G01N 2333/165* (2013.01); *G01N 2333/58* (2013.01); *G01N 2333/635* (2013.01)

(58) Field of Classification Search
None
See application file for complete search history.

(56) References Cited

U.S. PATENT DOCUMENTS

| | | |
|---|---|---|
| 2002/0081690 A1 | 6/2002 | Yamamoto et al. |
| 2006/0062783 A1 | 3/2006 | Roskos et al. |
| 2011/0190210 A1 | 8/2011 | Adini et al. |

FOREIGN PATENT DOCUMENTS

| | | |
|---|---|---|
| CN | 107255726 A | 10/2017 |
| EP | 1182213 A1 | 2/2022 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser: Boston, pp. 491-495.*
Skolnick et al. (2000). Trends in Biotech. 18(1):34-39.*
International Search Report and Written Opinion mailed Nov. 18, 2022 for International Application Serial No. PCT/US2022/033501 filed on Jun. 14, 2022.

\* cited by examiner

*Primary Examiner* — Christine J Saoud
*Assistant Examiner* — Jon M Lockard
(74) *Attorney, Agent, or Firm* — K&L Gates LLP; Louis C. Cullman; Michele Glasky Bergman

(57) ABSTRACT

An antigen with an increased half-life is provided for the formulation of more stable and consistent clinical diagnostic immunoassay controls and calibrators. An antigen analogue comprises a first and a second polypeptide which is identical or similar to corresponding terminal amino acid sequences of an antigen. The first and second polypeptides are connected with a PEG chain. Also provided are methods of calibrating assays using a compound disclosed herein.

9 Claims, 6 Drawing Sheets

Specification includes a Sequence Listing.

ANTIGEN ANALOGUE FOR CALIBRATION OF IMMUNOMETRIC DIAGNOSTIC ASSAYS

CROSS-REFERENCE TO RELATED APPLICATIONS

The present application claims the benefit of U.S. Provisional Patent Applications 63/210,904 filed Jun. 15, 2021 and 63/340,372 filed May 10, 2022, both of which are incorporated herein in their entirety.

BACKGROUND

Field

The present disclosure relates to immunometric diagnostic assays and materials for use thereof.

Discussion of Related Technology

In clinical diagnostic immunoassays, antibodies can be used to capture, detect, and quantify analytes in samples. The analytes may be antibodies, hormones, cofactors, or other compounds, and some classes of these analytes are generally referred to as antigens. The immunoassays require stable calibrators to generate accurate results over the shelf life of the assay. The immunoassays require stable controls to confirm accurate results over the shelf life of the assay. The controls and/or calibrators may be formulated with antigens derived from native, recombinant, or synthetic sources. However, many of these antigens are not stable and possess a very short half-life that makes their handling and analysis difficult. An antigen with an increased half-life would allow for the formulation of more stable and consistent clinical diagnostic immunoassay controls and calibrators.

SUMMARY

One aspect of the present disclosure provides a compound of formula (I):

wherein X is a first polypeptide,
wherein Y is a second polypeptide,
wherein n is between 1 and 30.

In the foregoing compound, X may have 3-30 amino acids. Y may have 3-30 amino acids. X may be RVEWLRKKLQDVHN (SEQ ID NO:1) or have at least 90% sequence identity with RVEWLRKKLQDVHN (SEQ ID NO:1). Y may be EDNVLVESH (SEQ ID NO:2) or have at least 90% sequence identity with EDNVLVESH (SEQ ID NO:2). X may be DLETSGLQEQRN (SEQ ID NO:3) or have at least 90% sequence identity with DLETSGLQEQRN (SEQ ID NO:3). Y may be PLQESPRPT (SEQ ID NO:4) or have at least 90% sequence identity with PLQESPRPT (SEQ ID NO:4). X may be GYYRRATRRIRGGDGKMKDLS (SEQ ID NO:5) or have at least 90% sequence identity with GYYRRATRRIRGGDGKMKDLS (SEQ ID NO:5). Y may be QRQKKQQTVTLLPAADLDDFS (SEQ ID NO:6) or have at least 90% sequence identity with QRQKKQQTVTLLPAADLDDFS (SEQ ID NO:6). In some embodiments, n may be between 5 and 10.

One aspect of the present disclosure provides a composition comprising the foregoing compound.

One aspect of the present disclosure provides a method of calibrating an immunometric diagnostic assay comprising measuring the intensity of light signals using the foregoing composition.

One aspect of the present disclosure provides a compound of formula (I):

wherein X is a first polypeptide which is RVEWLRKKLQDVHN (SEQ ID NO:1), DLETSGLQEQRN (SEQ ID NO:3), or GYYRRATRRIRGGDGKMKDLS (SEQ ID NO:5), or have at least 90% sequence identity with RVEWLRKKLQDVHN (SEQ ID NO:1), DLETSGLQEQRN (SEQ ID NO:3), or GYYRRATRRIRGGDGKMKDLS (SEQ ID NO:5);
wherein Y is a second polypeptide which is EDNVLVESH (SEQ ID NO:2), PLQESPRPT (SEQ ID NO:4), or QRQKKQQTVTLLPAADLDDFS (SEQ ID NO:6), or have at least 90% sequence identity with EDNVLVESH (SEQ ID NO:2), PLQESPRPT (SEQ ID NO:4), or QRQKKQQTVTLLPAADLDDFS (SEQ ID NO:6); and
wherein n is between 5 and 10.

One aspect of the present disclosure provides a composition comprising the foregoing compound.

One aspect of the present disclosure provides a method of calibrating an iPTH immunometric diagnostic assay, a NTproBNP immunometric diagnostic assay, or a SARS-CoV-2 immunometric diagnostic assay comprising measuring the intensity of light signals using the foregoing composition.

Also disclosed herein are compounds of formula (I):

wherein X is a first polypeptide selected from an amino acid sequence which has at least 95% sequence identity to RVEWLRKKLQDVHN (SEQ (ID NO:1), DLETSGLQEQRN (SEQ ID NO:3), or GYYRRATRRIRGGDGKMKDLS (SEQ ID NO:5), wherein Y is a second polypeptide, and wherein n is between 1 and 30. In some embodiments, X is RVEWLRKKLQDVHN (SEQ (ID NO:1), DLETSGLQEQRN (SEQ ID NO:3), or GYYRRATRRIRGGDGKMKDLS (SEQ ID NO:5).

Also disclosed herein are compounds of formula (I):

wherein X is a first polypeptide, wherein Y is a second polypeptide selected from an amino acid sequence which has at least 95% sequence identity to EDNVLVESH (SEQ ID NO:2), PLQESPRPT (SEQ ID NO:4), or QRQKKQQTVTLLPAADLDDFS (SEQ ID NO:6), and wherein n is between 1 and 30. In some embodiments, Y is EDNVLVESH (SEQ ID NO:2), PLQESPRPT (SEQ ID NO:4), or QRQKKQQTVTLLPAADLDDFS (SEQ ID NO:6).

In some embodiments, X has 6-25 amino acids. In some embodiments, Y has 6-25 amino acids. In some embodiments, n is between 1 and 8.

In some embodiments, Y is EDNVLVESH (SEQ ID NO:2), PLQESPRPT (SEQ ID NO:4), or QRQKKQQTVTLLPAADLDDFS (SEQ ID NO:6), or an amino acid sequence which has at least 95% sequence identity to EDNVLVESH (SEQ ID NO:2), PLQESPRPT (SEQ ID NO:4), or QRQKKQQTVTLLPAADLDDFS (SEQ ID NO:6).

In some embodiments, X is RVEWLRKKLQDVHN (SEQ ID NO:1) or an amino acid sequence which has at least 95% sequence identity to RVEWLRKKLQDVHN (SEQ ID NO:1) and is EDNVLVESH (SEQ ID NO:2) or an amino acid sequence which has at least 95% sequence identity to EDNVLVESH (SEQ ID NO:2).

In some embodiments, X is DLETSGLQEQRN (SEQ ID NO:3) or an amino acid sequence which has at least 95% sequence identity to DLETSGLQEQRN (SEQ ID NO:3) and Y is PLQESPRPT (SEQ ID NO:4) or an amino acid sequence which has at least 95% sequence identity to PLQESPRPT (SEQ ID NO:4).

In some embodiments, X is GYYRRATRRIR-GGDGKMKDLS (SEQ ID NO:5) or an amino acid sequence which has at least 95% sequence identity to GYYRRATRRIRGGDGKMKDLS (SEQ ID NO:5) and Y is QRQKKQQTVTLLPAADLDDFS (SEQ ID NO:6) or an amino acid sequence which has at least 95% sequence identity to QRQKKQQTVTLLPAADLDDFS (SEQ ID NO:6).

Also disclosed herein are compositions comprising a compound disclosed herein.

A method of calibrating an immunometric diagnostic assay comprising measuring the intensity of light signals using a compound or composition disclosed herein.

A method of calibrating an intact parathyroid hormone (iPTH) immunometric diagnostic assay comprising measuring the intensity of light signals using a compound or composition disclosed herein. In some embodiments, X is RVEWLRKKLQDVHN (SEQ ID NO:1) or an amino acid sequence which has at least 95% sequence identity to RVEWLRKKLQDVHN (SEQ ID NO:1) and is EDNVLVESH (SEQ ID NO:2) or an amino acid sequence which has at least 95% sequence identity to EDNVLVESH (SEQ ID NO:2).

A method of calibrating an N-terminal pro b-type natriuretic peptide (NTproBNP) immunometric diagnostic assay comprising measuring the intensity of light signals using a compound or composition disclosed herein. In some embodiments, X is DLETSGLQEQRN (SEQ ID NO:3) or an amino acid sequence which has at least 95% sequence identity to DLETSGLQEQRN (SEQ ID NO:3) and Y is PLQESPRPT (SEQ ID NO:4) or an amino acid sequence which has at least 95% sequence identity to PLQESPRPT (SEQ ID NO:4).

A method of calibrating a severe acute respiratory syndrome coronavirus 2 (SARS-CoV-2) immunometric diagnostic assay comprising measuring the intensity of light signals using a compound or composition disclosed herein. In some embodiments, X is GYYRRATRRIR-GGDGKMKDLS (SEQ ID NO:5) or an amino acid sequence which has at least 95% sequence identity to GYYRRATRRIRGGDGKMKDLS (SEQ ID NO:5) and Y is QRQKKQQTVTLLPAADLDDFS (SEQ ID NO:6) or an amino acid sequence which has at least 95% sequence identity to QRQKKQQTVTLLPAADLDDFS (SEQ ID NO:6).

DETAILED DESCRIPTION

Figure 1:
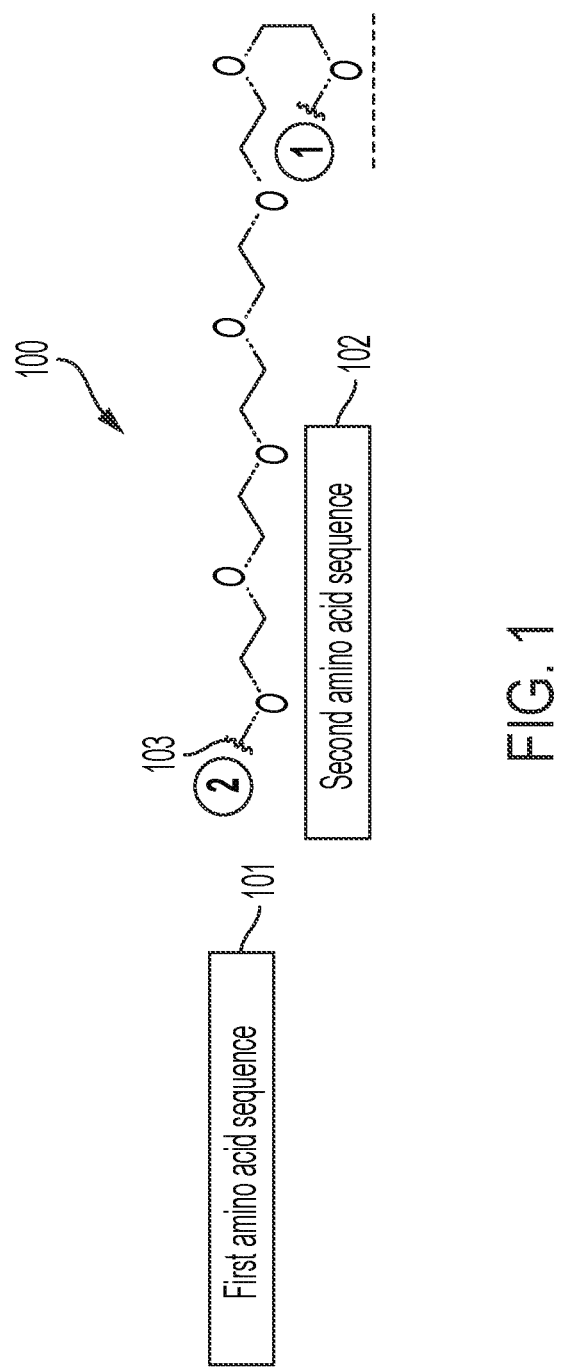
FIG. 1 is a chemical formula of an antigen analogue (iPTH analog) according to embodiments of the present disclosure.

Embodiments will now be described with reference to the accompanying drawings. The terminology used in the description presented herein is not intended to be interpreted in any limited or restrictive manner, simply because it is being utilized in conjunction with a detailed description of certain specific embodiments.

Antigen Analogue

This disclosure relates to antigen analogues that may be used instead of antigens for immunoassay controls and/or calibrators. The antigen analogues can produce a consistent and equivalent response in an assay, while possessing a longer half-life compared to the native, recombinant, or synthetic antigens that are commonly used as assay controls and/or calibrators. For example, analogues for a protein- or peptide-like antigen can have 1) amino acid sequences that are recognized by immunoassay antibodies or epitopes, and 2) a non-peptide, non-native bridge spacer portion that separates the two epitope portions and imparts greater stability than the original native polypeptide chain of the antigen.

PEG-Bridge Antigen Analogue

In some embodiments, an antigen analogue of protein- or peptide-like antigens can include one or more amino acid sequences that are recognized by immunoassay antibodies or epitopes, and a non-peptide, non-native bridge spacer chain linked to the amino acid sequences. In some embodiments, the antigen analogue may include two terminal amino acid sequences that are recognized by two immunoassay antibodies or epitopes, and a non-peptide bridging portion linking the two terminal amino acid sequences.

The non-peptide bridging portion may be more stable than polypeptides chemically or physically, such that degradation of the antigen analogues is minimized. The non-peptide bridging portion may not be degraded easily, and may not be hydrolyzed in the presence of peptidases or proteases.

At the same time, the non-peptide bridging portion may allow the antigen analogue to act in a similar fashion with protein- or peptide-like antigens that the antigen analogue is designed to replace. For example, the antigen analogue can overall have a chain length, molecular weight, hydrophilicity/hydrophobicity, or 3D-structure similar to the protein- or peptide-like antigens. In some embodiments, the non-peptide bridging portion may include a polyethylene glycol (PEG) chain. An antigen analogue having a PEG chain as non-peptide bridging portion may be referred to as a PEG-bridge antigen analogue herein. For example, the antigen analogue having two terminal sequences, a first polypeptide or amino acid sequence (X) and a second polypeptide or amino acid sequence (Y), and may have a structure represented by formula (I):

$$X-O-(CH_2CH_2O)_n-Y \quad (I)$$

The length of the PEG chain, or n of Formula 1, may vary, such that the antigen analogue acts in a similar fashion with protein- or peptide-like antigens that the antigen analogue is designed to replace. For example, the length of the PEG chain may be similar to the length of the corresponding peptide chain in the protein- or peptide-like antigen. In some embodiments, n of Formula 1 is between 1 and 30, 3 and 30, between 3 and 20, between 5 and 20, between 5 and 10, or between 6 and 9. In some embodiments, n is between 1 and 8.

The terminal amino acid sequences, the first and second polypeptide sequences, may be the same or similar to the corresponding amino acid sequences of the native protein- or peptide-like antigens. Each of the terminal amino acid sequences may have sufficient size or length to be recognized by immunoassay antibodies, or epitopes, while minimizing the length of the terminal amino acid sequences and maximizing the size of the non-peptide bridging portion can increase the stability of the antigen analogue. For example, each of the first and second polypeptide sequences may independently have 3-30 amino acids, 5-30 amino acids, 5-25 amino acids, 7-25 amino acids, 7-20 amino acids, or 10-20 amino acids. In some embodiments, each of the first and second polypeptide sequences may independently have 6-25 amino acids.

The PEG-bridge antigen analogue generates an assay signal while possessing a longer half-life than the native protein or peptide antigens. By replacing a large portion of the native antigen's amino acid structure with a PEG chain, the stability of the antigen analogue may be increased. For example, the PEG-bridge antigen analogue may degrade no more than 10% in some embodiments.

iPTH Antigen Analogue

In some embodiments, the PEG-bridge antigen analogue may be an analogue for the intact parathyroid hormone (iPTH) assay. Parathyroid hormone (PTH) is a single chain 84 amino acid polypeptide produced by the parathyroid gland. After PTH is secreted into the blood stream it undergoes extensive proteolysis to generate various fragments. In contrast to its degradation products, the concentration of intact PTH is relatively independent of glomerular filtration rate and reflects the biologically active portion of the hormone. In conjunction with serum calcium levels, the PTH assay may be used as an aid in the differential diagnosis of hypercalcemia, hypocalcemia, and parathyroid disorders. PTH determination is important in monitoring dialysis patients to manage renal osteodystrophy.

However, iPTH possesses a half-life that limits the handling and shelf life of calibrators and controls that are formulated with the synthetic peptide. Further, a native source of human iPTH is not commercially available due to instability.

FIG. 1 illustrates a structure of the PEG-bridge antigen analogue for iPTH 100 according to one embodiment. At each end, the PEG-bridge antigen analogue 100 has first and second amino acid sequences 101 and 102 to be recognized by immunoassay antibodies, or epitopes.

In the illustrated embodiment, the first end has the first amino acid sequence 101 (RVEWLRKKLQDVHN, SEQ ID NO:1). In some embodiments, the first amino acid sequence at the first end may have modifications (i.e. addition, deletion, and substitution) compared to the amino acid sequence RVEWLRKKLQDVHN (SEQ ID NO:1), wherein the modified amino acid sequence maintains the same activity, such as binding activity, as RVEWLRKKLQDVHN (SEQ ID NO:1). For example, the first amino acid sequence may be shorter or longer than the amino acid sequence RVEWLRKKLQDVHN (SEQ ID NO:1). The first amino acid sequence may have one or more substitutions to the amino acid sequence RVEWLRKKLQDVHN (SEQ ID NO:1). In some embodiments, the first amino acid sequence may be 70%, 80%, 90%, 95%, 96%, 97%, 98%, 99% or greater sequence identity to the amino acid sequence RVEWLRKKLQDVHN (SEQ ID NO:1). In some embodiments, the first amino acid sequence comprises RVEWLRKKLQDVHN (SEQ ID NO:1) with one, two, or three conservative amino acid substitutions.

Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

In the illustrated embodiment, the second end has the second amino acid sequence 102 (EDNVLVESH, SEQ ID NO:2). In some embodiments, the second amino acid sequence at the second end may have modifications (i.e. addition, deletion, and substitution) compared to the amino acid sequence EDNVLVESH (SEQ ID NO:2), wherein the modified amino acid sequence maintains the same activity, such as binding activity, as EDNVLVESH (SEQ ID NO:2). For example, the second amino acid sequence may be shorter or longer than the amino acid sequence EDNVLVESH (SEQ ID NO:2). The second amino acid sequence may have one or more substitutions to the amino acid sequence EDNVLVESH (SEQ ID NO:2). In some embodiments, the second amino acid sequence may be 70%, 80%, 90%, 95%, 96%, 97%, 98%, 99%, or greater sequence identity to the amino acid sequence EDNVLVESH (SEQ ID NO:2). In some embodiments, the second amino acid sequence comprises EDNVLVESH (SEQ ID NO:2) with one, two, or three conservative amino acid substitutions.

In the illustrated embodiment, the PEG bridging portion 103 includes 7 monomers. In some embodiments, the number of monomers of the PEG bridging portion 103 may be between 1 and 40, between 1 and 30, between 1 and 20, or between 1 and 10. In some embodiments, the number of monomers in the PEG bridging portion is between 1 and 8.

Also disclosed herein is use of iPTH analogue 100 in an iPTH immunometric diagnostic assay, for example the VITROS® Intact PTH II assay (Ortho-Clinical Diagnostics, Inc.).

NT-proBNP Antigen Analogue

B-type natriuretic peptide (BNP) is a hormone produced by the heart. N-terminal (NT)-pro hormone BNP (NT-proBNP) is a non-active prohormone that is released from the same molecule that produces BNP. Both BNP and NT-proBNP are released in response to changes in pressure inside the heart.

Figure 4:
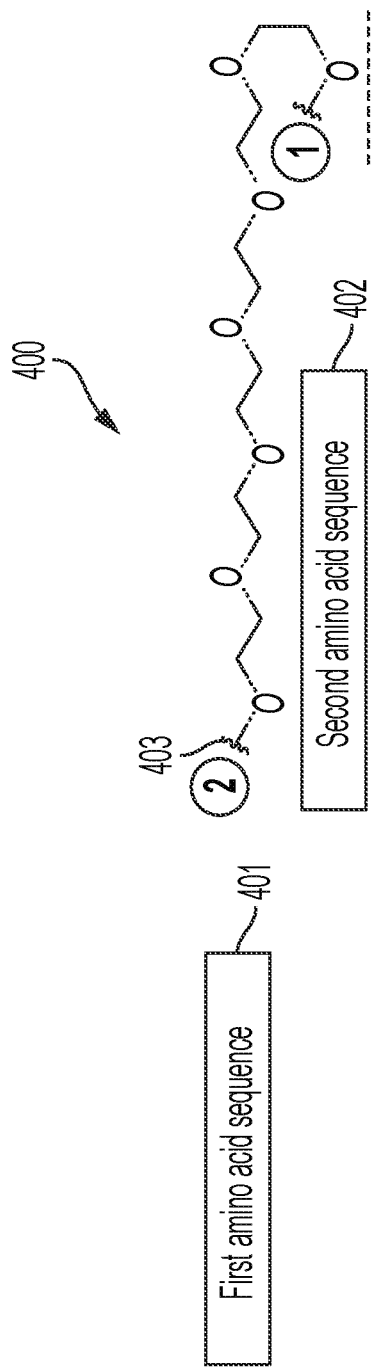
FIG. 4 is a chemical formula of an antigen analogue (NTproBNP analog) according to embodiments of the present disclosure.

FIG. 4 illustrates a structure of the PEG-bridge antigen analogue for NT-proBNP 400 according to one embodiment. At each end, the PEG-bridge antigen analogue 400 has first and second amino acid sequences 401 and 402 to be recognized by immunoassay antibodies, or epitopes.

In the illustrated embodiment, the first end has the first amino acid sequence 401 (DLETSGLQEQRN, SEQ ID NO:3). In some embodiments, the first amino acid sequence at the first end may have modifications (i.e. addition, deletion, and substitution) compared to the amino acid sequence DLETSGLQEQRN (SEQ ID NO:3), wherein the modified amino acid sequence maintains the same activity, such as binding activity, as DLETSGLQEQRN (SEQ ID NO:3). For example, the first amino acid sequence may be shorter or longer than the amino acid sequence DLETSGLQEQRN (SEQ ID NO:3). The first amino acid sequence may have one or more substitutions to the amino acid sequence DLETSGLQEQRN (SEQ ID NO:3). In some embodiments, the first amino acid sequence may be 70%, 80%, 90%, 95%, 96%, 97%, 98%, 99%, or greater sequence identity to the amino acid sequence DLETSGLQEQRN (SEQ ID NO:3). In some embodiments, the first amino acid sequence comprises DLETSGLQEQRN (SEQ ID NO:3) with one, two, or three conservative amino acid substitutions.

In the illustrated embodiment, the second end has the second amino acid sequence 402 (PLQESPRPT, SEQ ID NO:4). In some embodiments, the second amino acid sequence at the second end may have modifications (i.e. addition, deletion, and substitution) compared to the amino acid sequence PLQESPRPT (SEQ ID NO:4), wherein the modified amino acid sequence maintains the same activity, such as binding activity, as PLQESPRPT (SEQ ID NO:4). For example, the second amino acid sequence may be shorter or longer than the amino acid sequence PLQESPRPT (SEQ ID NO:4). The second amino acid sequence may have one or more substitutions to the amino acid sequence PLQESPRPT (SEQ ID NO:4). In some embodiments, the second amino acid sequence may be 70%, 80%, 90%, 95%, 96%, 97%, 98%, 99%, or greater sequence identity to the amino acid sequence PLQESPRPT (SEQ ID NO:4). In some embodiments, the second amino acid sequence comprises PLQESPRPT (SEQ ID NO:4) with one, two, or three conservative amino acid substitutions.

In the illustrated embodiment, the PEG bridging portion 403 includes 7 monomers. In some embodiments, the number of monomers of the PEG bridging portion 403 may be between 1 and 40, between 1 and 30, between 1 and 20, or between 1 and 10. In some embodiments, the number of monomers in the PEG bridging portion is between 1 and 8.

Also disclosed herein is use of NT-proBNP analogue 400 in an NT-proBNP immunometric diagnostic assay, for example the VITROS® NTproBNP II immunodiagnostic assay (Ortho-Clinical Diagnostics, Inc.).

SARS-CoV-2 Nucleocapsid Antigen Analogue

Figure 6:
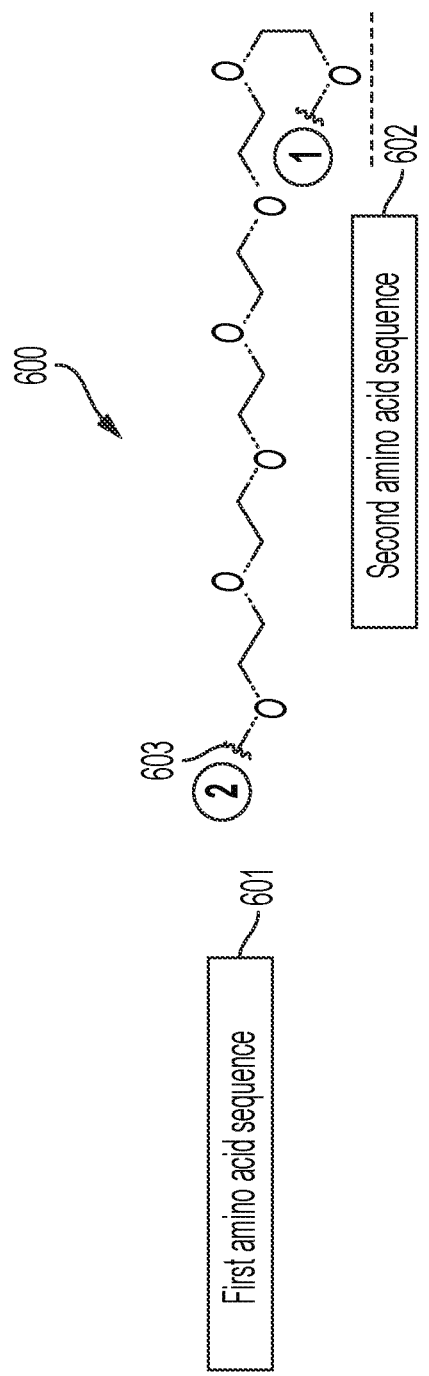
FIG. 6 is a chemical formula of an antigen analogue (SARS-CoV-2 analog) according to embodiments of the present disclosure.

FIG. 6 illustrates a structure of the PEG-bridge antigen analogue for SARS-CoV-2 (Covid-19, 2019-nCoV) nucleocapsid 600 according to one embodiment. At each end, the PEG-bridge antigen analogue 600 has first and second amino acid sequences 601 and 602 to be recognized by immunoassay antibodies, or epitopes.

At least one of the first and second amino acid sequences 601, 602 may be an epitope for a monoclonal antibody from SARS-CoV-2. In some embodiments, each of the first and second amino acid sequences 601, 602 may be monoclonal antibody epitopes. For example, the first amino acid sequence 601 and/or the second amino acid sequence 602 may be an epitope for one or more monoclonal antibodies selected from the group consisting of R001, MM05, R004, T30, MM163, MM184, MM137, R957, RC02, MM08, T62, R019, MM181, MM187, MM124, R004, MM182, MM186, R0006, R040, MM123, or any other known monoclonal antibodies for SARS-CoV-2.

In some embodiments, the first amino acid sequence 601 includes the epitope for the monoclonal antibody MM05 from SARS-CoV-2, or a portion thereof. For example, the first amino acid sequence 601 may be (GYYRRATRRIR-GGDGKMKDLS, SEQ ID NO:5). In some embodiments, the first amino acid sequence 601 at the first end may have modifications (i.e. addition, deletion, and substitution) compared to the amino acid sequence GYYRRATRRIR-GGDGKMKDLS (SEQ ID NO:5), wherein the modified amino acid sequence maintains the same activity, such as binding activity, as GYYRRATRRIRGGDGKMKDLS (SEQ ID NO:5). For example, the first amino acid sequence 601 may be shorter or longer than the amino acid sequence GYYRRATRRIRGGDGKMKDLS (SEQ ID NO:5). The first amino acid sequence may have one or more substitutions to the amino acid sequence GYYRRATRRIR-GGDGKMKDLS (SEQ ID NO:5). In some embodiments, the first amino acid sequence may be 70%, 80%, 90%, 95%, 96%, 97%, 98%, 99%, or greater sequence identity to the amino acid sequence GYYRRATRRIRGGDGKMKDLS (SEQ ID NO:5). In some embodiments, the first amino acid sequence comprises GYYRRATRRIRGGDGKMKDLS (SEQ ID NO:5) with one, two, or three conservative amino acid substitutions.

In some embodiments, the second end includes the epitope for the monoclonal antibody R001 from SARS-CoV-2, or a portion thereof. For example, the second amino acid sequence 602 may be (QRQKKQQTVTLL-PAADLDDFS, SEQ ID NO:6). In some embodiments, the second amino acid sequence at the second end may have modifications (i.e. addition, deletion, and substitution) compared to the amino acid sequence QRQKKQQTVTLL-PAADLDDFS (SEQ ID NO:6), wherein the modified amino acid sequence maintains the same activity, such as binding activity, as QRQKKQQTVTLLPAADLDDFS (SEQ ID NO:6). For example, the second amino acid sequence may be shorter or longer than the amino acid sequence QRQKKQQTVTLLPAADLDDFS (SEQ ID NO:6). The second amino acid sequence may have one or more substitutions to the amino acid sequence QRQKKQQTVTLL-PAADLDDFS (SEQ ID NO:6). In some embodiments, the second amino acid sequence may be 70%, 80%, 90%, 95%, 96%, 97%, 98%, 99%, or greater sequence identity to the amino acid sequence QRQKKQQTVTLLPAADLDDFS (SEQ ID NO:6). In some embodiments, the second amino acid sequence comprises QRQKKQQTVTLLPAADLDDFS (SEQ ID NO:6) with one, two, or three conservative amino acid substitutions.

In the illustrated embodiment, the PEG bridging portion 603 includes 7 monomers. In some embodiments, the number of monomers of the PEG bridging portion 603 may be between 1 and 40, between 1 and 30, between 1 and 20, or between 1 and 10. In some embodiments, the number of monomers in the PEG bridging portion is between 1 and 8.

Also disclosed herein is use of SARS-CoV-2 analogue 600 in an SARS-CoV-2 immunometric diagnostic assay, for example the VITROS® SARS-CoV-2 Antigen Test (Ortho-Clinical Diagnostics, Inc.).

Methods of Using PEG-Bridge Antigen Analogues

Also disclosed herein are immunoassay methods which involve the simultaneous reaction of analyte (an antigen) present in the sample with a biotinylated antibody and a horseradish peroxidase (HRP)-labeled antibody conjugate. The antigen-antibody complex is captured by streptavidin coated on a solid substrate (wells). Unbound materials are removed by washing. The bound HRP conjugate is measured by a luminescent reaction. The light signals are indicative of the amount of HRP-conjugate bound which is directly proportional to the concentration of analyte present.

The disclosed immunoassay are calibrated using the antigen analogues disclosed herein and are added to samples or buffers in known quantities to function as a calibrator or control for the assay.

EXAMPLES

Example 1

The VITROS® Intact PTH II assay (Ortho-Clinical Diagnostics, Inc.), an immunometric immunoassay technique was used which involves the simultaneous reaction of PTH (as an antigen) present in the sample with a biotinylated antibody (goat polyclonal anti-PTH39-84) and a horseradish peroxidase (HRP)-labeled antibody conjugate (goat polyclonal anti-PTH1-34). The antigen-antibody complex was captured by streptavidin coated on a solid substrate (wells). Unbound materials were removed by washing. The bound HRP conjugate was measured by a luminescent reaction. A reagent containing luminogenic substrates (a luminol derivative and a peracid salt) and an electron transfer agent, was added to the coated substrate. The HRP in the bound conjugate catalyzed the oxidation of the luminol derivative, producing light. The electron transfer agent (a substituted acetanilide) increased the level of light produced and prolongs its emission. The light signals were read by the system. The amount of HRP conjugate bound was directly proportional to the concentration of PTH present.

Figure 2:
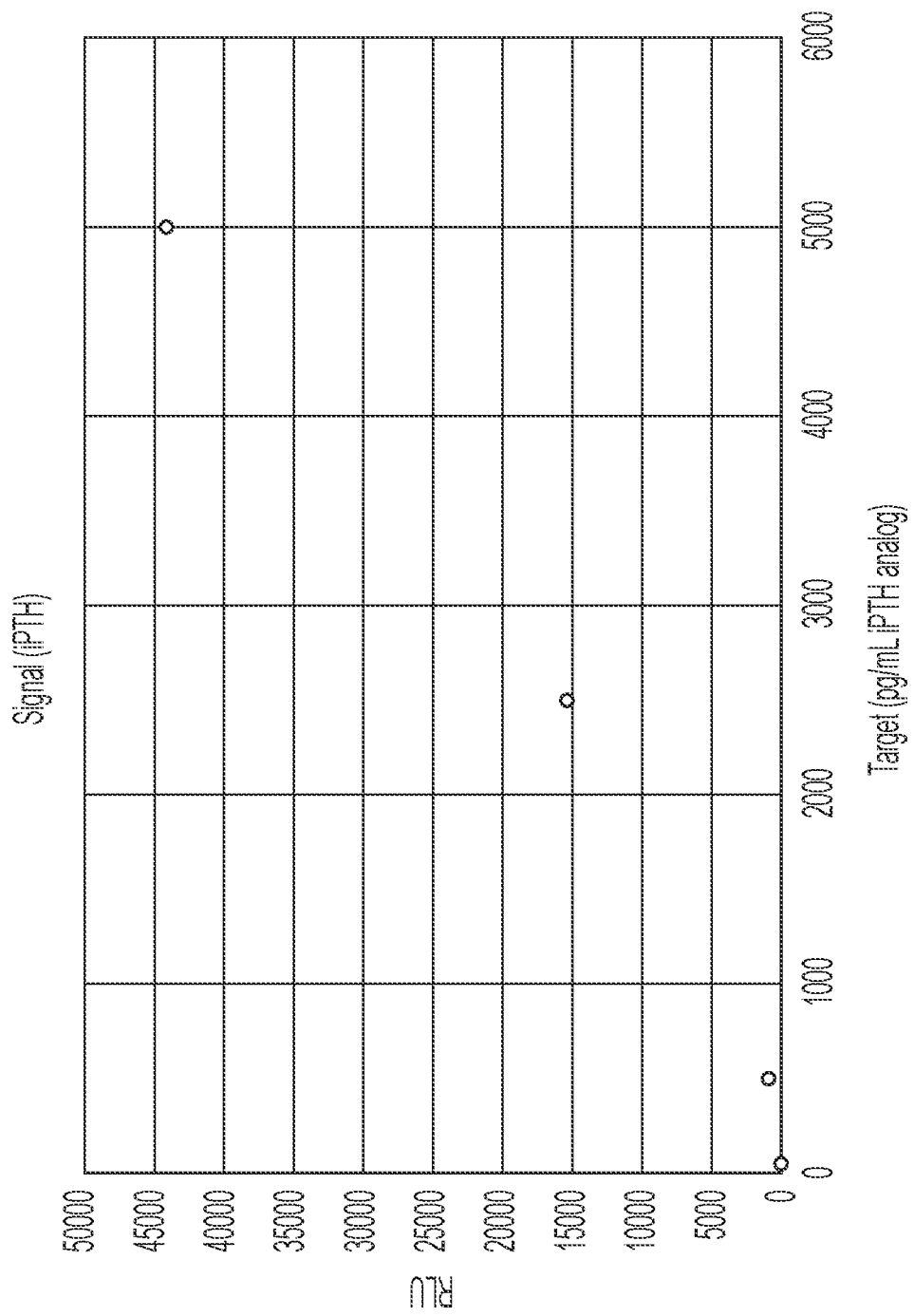
FIG. 2 is a graph illustrating the intensity of light signal at different target concentrations of an antigen analogue according to embodiments of the present disclosure.

FIG. 2 illustrates the intensity of light signals (in relative light units (RLU)) read by VITROS® Immunodiagnostic ECi platform (Ortho-Clinical Diagnostics) using the PEG-bridge antigen analogue 100 of FIG. 1, at different targeted concentrations (i.e. 50 pg/mL, 500 pg/mL, 2500 pg/mL, and 5000 pg/mL) in buffer with bovine serum albumin and an antimicrobial agent. With 50 pg/mL of PEG-bridge antigen analogue 100, 4.788995 RLU were detected. With 500 pg/mL of PEG-bridge antigen analogue 100, 902.34 RLU were detected. With 2500 pg/mL of PEG-bridge antigen analogue 100, 15386.346 RLU were detected. With 5000 pg/mL of PEG-bridge antigen analogue 100, 44121.512 RLU were detected. From these, it was confirmed that the PEG-bridge antigen analogue 100 can generate a signal proportional to its concentration in the VITROS® Intact PTH II assay.

Example 2

Figure 3:
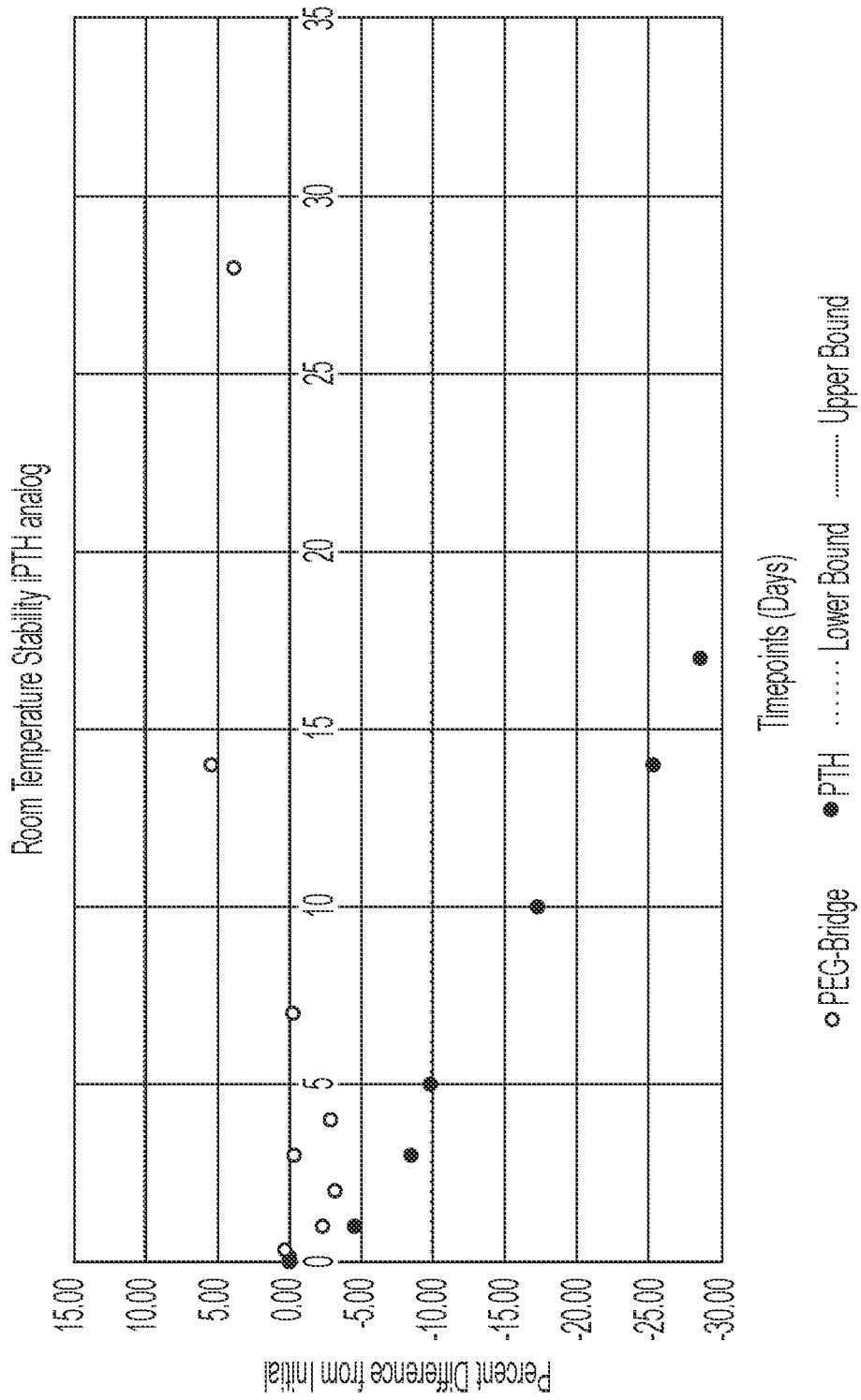
FIG. 3 is a graph illustrating the change of the concentration of a synthetic iPTH and an antigen analogue according to embodiments of the present disclosure.

The stability of the PEG-bridge antigen analogue 100 and a synthetic iPTH antigen over time were measured. A solution including the PEG-bridge antigen analogue 100, and another solution including a synthetic iPTH antigen in a standard buffer were prepared. The solutions were kept at ambient temperature (~23° C.). Concentrations of the PEG-bridge antigen analogue 100 and the synthetic iPTH antigen were measured over time. FIG. 3 illustrates the change of predicted concentrations (%) of the PEG-bridge antigen analogue 100 and the native sequence of synthetic iPTH antigen over time. As shown in FIG. 3, the synthetic iPTH antigen showed decrease of concentration by 10% after 5 days, while the PEG-bridge antigen analogue 100 showed no significant change in concentration after 28 days. It was confirmed that the PEG-bridge antigen analogue 100 does not degrade significantly over time, and is more stable than the synthetic iPTH antigen.

Example 3

The reproducibility of the sample containing the PEG-bridge antigen analogue 100 was measured. Two replicates of each of 4 samples having different concentrations (30 pg/mL; 100 pg/mL, 500 pg/mL, 1500 pg/mL) were tested on two separate occasions per day on at least 20 different days, and the data is shown in Table 2.

In Table 2, "% CV w/in Run" represents between-duplicate precision averaged over all runs, in form of coefficient of variance (%). "% CV w/in Cal" represents total precision with weighted components of within-run, between-run and between-day variation, in form of variance (%). "% CV w/in Lab" represents a measure of the effect of recalibration on total precision, calculated within reagent lot, using data from at least 4 calibrations. As shown in Table 2, the sample containing PEG-bridge antigen analogue 100 showed high precision in all concentrations, exhibiting lower than 4% CV in all three measures.

TABLE 2

| Target Concentration (pg/mL) | % CV w/in Run | % CV w/in Cal | % CV w/in Lab |
|---|---|---|---|
| 30 | 1.4 | 2.6 | 2.3 |
| 100 | 1.6 | 2.2 | 1.9 |
| 500 | 1.2 | 2.0 | 1.5 |
| 1500 | 1.2 | 3.8 | 3.7 |

Example 4

Figure 5:
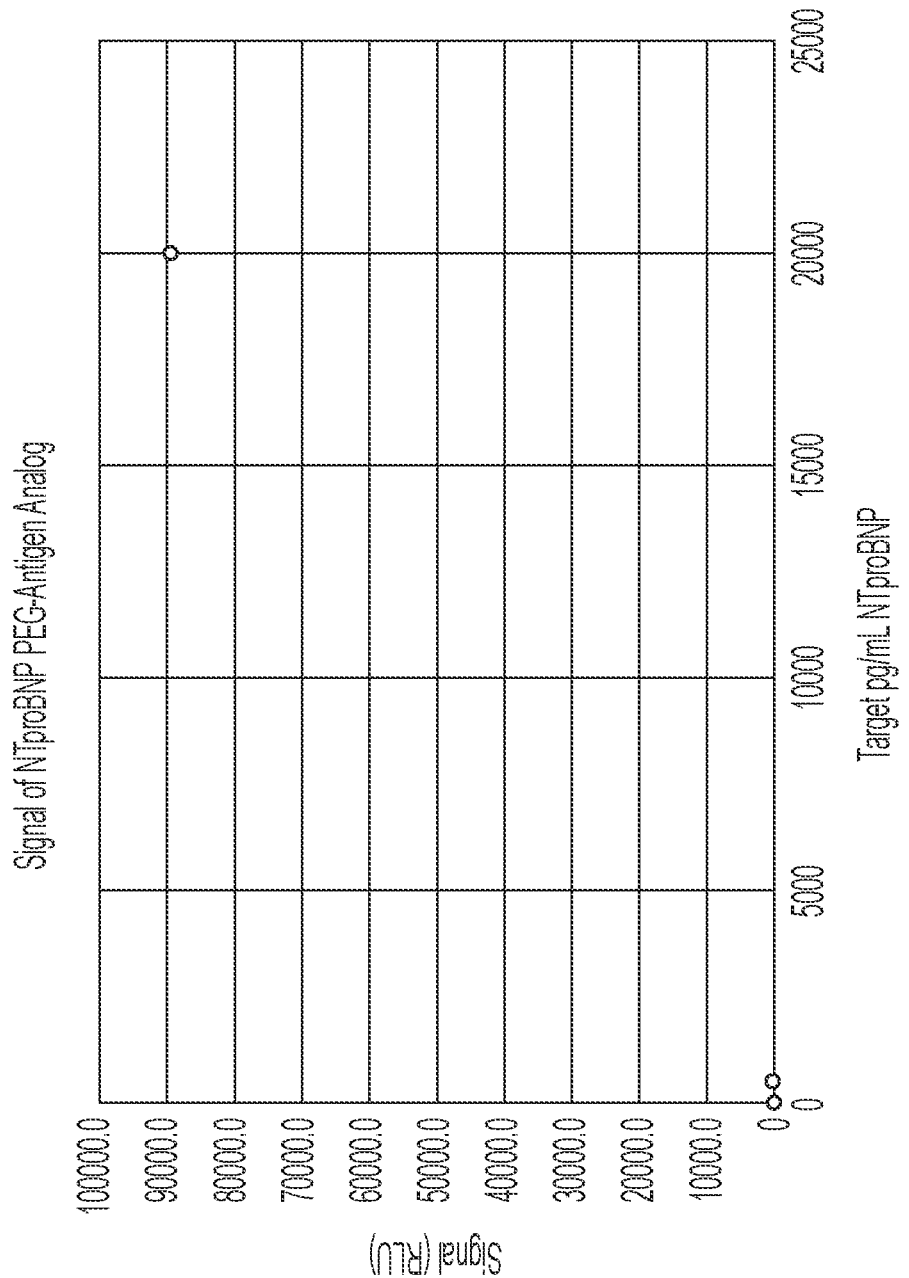
FIG. 5 is a graph illustrating the intensity of light signal at different target concentrations of an antigen analogue according to embodiments of the present disclosure.

A PEG-bridge antigen analogue 400 (FIG. 4) for N-terminal pro b-type natriuretic peptide (NTproBNP), having a PEG-bridge portion and two terminal polypeptides, resembling NTproBNP linked by the PEG-bridge portion was prepared. PEG-bridge antigen analogue 400 samples with target concentration of 500 pg/ml and 20000 pg/ml were prepared and used for the VITROS® NTproBNP II immunodiagnostic assay (Ortho-Clinical Diagnostics). FIG. 5 illustrates the light signal, in RLU, of these samples. As shown in FIG. 5, the PEG-bridge analogue 400 of NTproBNP generated 244.5 RLU at 500 pg/mL, and 89478.6 RLU at 20000 pg/mL.

Example 5

The PEG-bridge antigen analogue 600 (FIG. 6) for SARS-CoV-2 having (GYYRRATRRIRGGDGKMKDLS; SEQ ID NO:5) as the first amino acid sequence and (QRQKKQQTVTLLPAADLDDFS; SEQ ID NO:6) as the second amino acid sequence was prepared. Then the PEG-bridge antigen analogue 600 was dissolved in phosphate buffered saline (PBS) to the concentration of 0.016 pg/mL.

In order to determine stability, the PEG-bridge antigen analogue 600 solutions were stored for 1, 2, 3, 4, or 5 days at 37° C. or 1, 2, 3, 4, or 5 days at 25° C.

Solid substrate wells were coated with 1.5 μg/mL SARS-CoV/SARS-CoV-2 nucleocapsid antibody R001 (rabbit monoclonal) (Sino Biological, CAT #40143-R001), and incubated with a 0.016 μg/mL solution of the PEG-bridge antigen analogue 600 for 30 min at 37° C. After wash, the wells were incubated with SARS-CoV/SARS-CoV-2 nucleocapsid antibody MM05 (mouse monoclonal) at 0.016 ug/mL (Sino Biological, CAT #40143-MM05) for 30 min at 37° C., followed by washing and incubation with HRP-donkey anti-mouse IgG (H+L) (Jackson Immuno Research Lab, CAT #715-035-150).

The experiment above was repeated using 2 μg/mL SARS-CoV-2 nucleocapsid protein (GenScript, Cat. No. Z03488) solution in PBS instead of the PEG-bridge antigen analogue 600.

The experiment above was repeated with 0.08 μg/mL SARS-CoV-2 (2019-nCoV) Nucleocapsid-His Recombinant Protein (SinoBiological, Cat. No. 40588-V07E) solution in PBS instead of the PEG-bridge antigen analogue 600.

After incubation, the wells were washed and added with chemiluminescent signal reagents. Then the reactivity was measured by Molecular Device i3x Multi-mode plate reader and relative light units (RLU) were determined. The results are shown in Tables 3-6 below:

TABLE 3

Relative Luminescence Light Unit (RLU)

| Antigen | Stored for 0 days (37° C.) | Stored for 1 days (37° C.) | Stored for 2 days (37° C.) | Stored for 3 days (37° C.) | Stored for 4 days (37° C.) | Stored for 5 days (37° C.) |
|---|---|---|---|---|---|---|
| SARS-CoV-2 Nucleocapsid protein (2 μg/mL) | 9,835 | 5,409 | 7,779 | 4,545 | 5,745 | 4,320 |
| SARS-CoV-2 Nucleocapsid-His Recombinant Protein ((0.08 μg/mL) | 11,611 | 9,289 | 9,010 | 8,728 | 7,160 | 7,458 |
| PEG-bridge antigen analogue 600 (0.016 μg/mL) | 13,526 | 14,094 | 13,174 | 13,118 | 13,723 | 12,771 |

TABLE 4

Reactivity Change versus 0 days

| Antigen | Stored for 0 days (37° C.) | Stored for 1 days (37° C.) | Stored for 2 days (37° C.) | Stored for 3 days (37° C.) | Stored for 4 days (37° C.) | Stored for 5 days (37° C.) |
|---|---|---|---|---|---|---|
| SARS-CoV-2 Nucleocapsid protein (2 μg/mL) | 0% | −45% | −38% | −68% | −90% | −96% |
| SARS-CoV-2 Nucleocapsid-His Recombinant Protein (0.08 μg/mL) | 0% | −20% | −28% | −32% | −51% | −58% |
| PEG-bridge antigen analogue 600 (0.016 μg/mL) | 0% | 4.2% | −2.5% | −3.1% | 1.5% | −5.5% |

TABLE 5

Relative Luminescence Light Unit (RLU)

| Antigen | Stored for 0 days (25° C.) | Stored for 1 days (25° C.) | Stored for 2 days (25° C.) | Stored for 3 days (25° C.) | Stored for 4 days (25° C.) | Stored for 5 days (25° C.) |
|---|---|---|---|---|---|---|
| SARS-CoV-2 Nucleocapsid protein (2 μg/mL) | 9,835 | 8,360 | 7,996 | 7,036 | 7,302 | 6,476 |
| SARS-CoV-2 Nucleocapsid-His Recombinant Protein (0.08 μg/mL) | 11,611 | 11,007 | 10,180 | 9,473 | 8,959 | 8,744 |
| PEG-bridge antigen analogue 600 (0.016 μg/mL) | 13,526 | 13,688 | 13,375 | 13,727 | 13,238 | 12,930 |

TABLE 6

Reactivity Change versus 0 days

| Antigen | Stored for 0 days (25° C.) | Stored for 1 days (25° C.) | Stored for 2 days (25° C.) | Stored for 3 days (25° C.) | Stored for 4 days (25° C.) | Stored for 5 days (25° C.) |
|---|---|---|---|---|---|---|
| SARS-CoV-2 Nucleocapsid protein (2 μg/mL) | 0% | −15% | −22% | −35% | −36% | −46% |
| SARS-CoV-2 Nucleocapsid-His Recombinant Protein (0.08 μg/mL) | 0% | −5.2% | −13% | −21% | −28% | −32% |
| PEG-bridge antigen analogue 600 (0.016 μg/mL) | 0% | 1.2% | −1.1% | 1.5% | −2.1% | −4.5% |

As demonstrated in Tables 3 through 6, native and recombinant SARS-CoV-2 nucleocapsid proteins were observed to be labile at ambient temperatures (25° C.), degrading up to 46% over 5 days as determined by immunoassay luminescence. However, the PEG-bridge antigen analog demonstrated less than 5% degradation over the same timeframe and conditions. This established that the PEG-bridge format of antigen possesses robust stability when compared to native or recombinant preparations.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" mean within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A compound of formula (I):

$$X—O—(CH_2CH_2O)_n—Y \quad (I)$$

wherein (i) X is RVEWLRKKLQDVHN (SEQ ID NO:1) and Y is EDNVLVESH (SEQ ID NO:2), (ii) X is DLETSGLQEQRN (SEQ ID NO:3) and Y is PLQESPRPT (SEQ ID NO:4), or (iii) X is GYYRRATRRIRGGDGKMKDLS (SEQ ID NO:5) and Y is QRQKKQQTVTLLPAADLDDFS (SEQ ID NO:6), and n is an integer between 1 and 30.

2. The compound of claim 1, wherein X is RVEWLRKKLQDVHN (SEQ ID NO:1) and Y is EDNVLVESH (SEQ ID NO:2).

3. The compound of claim 1, wherein X is DLETSGLQEQRN (SEQ ID NO:3) and Y is PLQESPRPT (SEQ ID NO:4).

4. The compound of claim 1, wherein X is GYYRRATRRIRGGDGKMKDLS (SEQ ID NO:5) and Y is QRQKKQQTVTLLPAADLDDFS (SEQ ID NO:6).

5. The compound of claim 1, wherein n is an integer between 1 and 8.

6. A method of calibrating an immunometric diagnostic assay comprising measuring the intensity of light signals using the compound of claim 1.

7. The method of claim 6, wherein the assay is an intact parathyroid hormone (iPTH) immunometric diagnostic assay wherein X is RVEWLRKKLQDVHN (SEQ ID NO:1) and Y is EDNVLVESH (SEQ ID NO:2).

8. The method of claim 6, wherein the assay is an N-terminal pro b-type natriuretic peptide (NTproBNP) immunometric diagnostic assay, wherein X is DLETSGLQEQRN (SEQ ID NO:3) and Y is PLQESPRPT (SEQ ID NO:4).

9. The method of claim 6, wherein the assay is a severe acute respiratory syndrome coronavirus 2 (SARS-CoV-2) immunometric diagnostic assay, wherein X is GYYRRATRRIRGGDGKMKDLS (SEQ ID NO:5) and Y is QRQKKQQTVTLLPAADLDDF (SEQ ID NO:6).

* * * * *

SEQUENCE LISTING

```
<160> NUMBER OF SEQ ID NOS: 6

<210> SEQ ID NO 1
<211> LENGTH: 14
<212> TYPE: PRT
<213> ORGANISM: Homo sapiens

<400> SEQUENCE: 1

Arg Val Glu Trp Leu Arg Lys Lys Leu Gln Asp Val His Asn
1               5                   10

<210> SEQ ID NO 2
<211> LENGTH: 9
<212> TYPE: PRT
<213> ORGANISM: Homo sapiens

<400> SEQUENCE: 2

Glu Asp Asn Val Leu Val Glu Ser His
1               5
```

-continued

<210> SEQ ID NO 3
<211> LENGTH: 12
<212> TYPE: PRT
<213> ORGANISM: Homo sapiens

<400> SEQUENCE: 3

Asp Leu Glu Thr Ser Gly Leu Gln Glu Gln Arg Asn
1 5 10

<210> SEQ ID NO 4
<211> LENGTH: 9
<212> TYPE: PRT
<213> ORGANISM: Homo sapiens

<400> SEQUENCE: 4

Pro Leu Gln Glu Ser Pro Arg Pro Thr
1 5

<210> SEQ ID NO 5
<211> LENGTH: 21
<212> TYPE: PRT
<213> ORGANISM: Homo sapiens

<400> SEQUENCE: 5

Gly Tyr Tyr Arg Arg Ala Thr Arg Arg Ile Arg Gly Gly Asp Gly Lys
1 5 10 15

Met Lys Asp Leu Ser
20

<210> SEQ ID NO 6
<211> LENGTH: 21
<212> TYPE: PRT
<213> ORGANISM: Homo sapiens

<400> SEQUENCE: 6

Gln Arg Gln Lys Lys Gln Gln Thr Val Thr Leu Leu Pro Ala Ala Asp
1 5 10 15

Leu Asp Asp Phe Ser
20